(12) United States Patent
Kempter et al.

(10) Patent No.: US 8,648,091 B2
(45) Date of Patent: Feb. 11, 2014

(54) DIHYDROQUINOLINONES AS ECTOPARASITICIDES

(75) Inventors: Christoph Kempter, Basel (CH); Ulrich Roos, Lörrach (DE); Sandra Schorderet Weber, Neuchâtel (CH); Yvonne Ebinger, Freiburg (DE); Silvia Glaser, Breisach (DE)

(73) Assignee: Novartis AG, Basel (CH)

( * ) Notice: Subject to any disclaimer, the term of this patent is extended or adjusted under 35 U.S.C. 154(b) by 34 days.

(21) Appl. No.: 12/740,869

(22) PCT Filed: Nov. 6, 2008

(86) PCT No.: PCT/EP2008/065033
§ 371 (c)(1),
(2), (4) Date: Apr. 30, 2010

(87) PCT Pub. No.: WO2009/060015
PCT Pub. Date: May 14, 2009

(65) Prior Publication Data
US 2010/0249173 A1    Sep. 30, 2010

(30) Foreign Application Priority Data
Nov. 9, 2007 (EP) .................................. 07120324

(51) Int. Cl.
*A61K 31/44*    (2006.01)
*A61K 31/47*    (2006.01)

(52) U.S. Cl.
USPC .......................................... 514/291; 514/312

(58) Field of Classification Search
None
See application file for complete search history.

(56) References Cited

FOREIGN PATENT DOCUMENTS

| WO | WO 02/26713 | * | 4/2002 | ........... A07D 215/18 |
|----|-------------|---|--------|----------------------|
| WO | WO 02/26713 A1 | | 4/2002 | |
| WO | WO 2006/059400 | * | 6/2006 | ............. A61K 31/47 |
| WO | WO 2006/059400 A1 | | 6/2006 | |

OTHER PUBLICATIONS

Uchida et al (J Antibiot 59:646-651, 2006).*
Alkofahi et al (Insecticides of Plant Origin, Chapter 3, pp. 25-43, 1989).*
ISR, Mar. 23, 2009.
Written Opinion, Apr. 1, 2009.

* cited by examiner

*Primary Examiner* — Craig Ricci
(74) *Attorney, Agent, or Firm* — Ann R. Pokalsky, Esq.; Dilworth & Barrese, LLP

(57) ABSTRACT

Disclosed are uses of dihydroquinolinone derivatives for combating ectoparasites on non-human animals. Example ectoparasites include, for example, representatives of the order acarina, including ticks and mites. Also disclosed are compositions containing dihydroquinolinone derivatives.

3 Claims, No Drawings

DIHYDROQUINOLINONES AS ECTOPARASITICIDES

CROSS-REFERENCE TO RELATED APPLICATIONS

This application claims priority to PCT Application Number PCT/EP2008/065033, filed Nov. 6, 2008, which claims priority to EP Application Number 07120324.4, filed Nov. 9, 2007.

The present invention is based on the discovery of the pronounced acaricidal activity of the dihydroquinolinone derivatives as defined hereinafter in formula I. The invention relates to use of a dihydroquinolinone derivative of formula I for combating ectoparasites on non-human animals. Ectoparasites include insects, acarina and especially ticks. It further relates to ectoparasiticidal compositions containing such a dihydroquinolinone derivative, a method of controlling ectoparasites, whereby an effective amount of at least one dihydroquinolinone derivative of formula I is administered to the habitat of the parasite, the use of dihydroquinolinone derivative of the formula I for the preparation of an ectoparasiticidal, more preferably insecticidal or acaricidal composition and especially a tickicidal composition and their use for the preparation of a veterinary composition for the treatment of said ectoparasites on non-human animals, and last but not least the use of a compound of the formula I in the manufacture of a veterinary medicament for combating said ectoparasites.

Dihydroquinolinone derivatives are known natural compounds that have been published under different names, such as Dihydroquinolinones, Quinolinones, Penigequinolones, Peniprequinolone, Yaequinolones, Aspoquinolones or FKI-2140 derivatives.

In the following the name dihydroquinolinone derivatives will be used. They can be prepared in accordance with the preparation processes described in the literature. Certain Dihydroquinolinone derivatives were isolated from the culture broth of *Penicillium* sp. FKI-2140 (Ryuji Uchida et al., 'Yaequinolones, New Insecticidal Antibiotics Produced by *Penicillium* sp. FKI-2140', J. Antibiot. 59(10): 646-658 (2006); and WO2006/059400) or by the fungus *Penicillium* cf. *simplicissimum* (Miyako Kusano et al., 'Nematicidal Alkaloides and Related Compounds Produced by the Fungus *Penicillium* cf. *simplicissimum*. Biosci. Biotechnol. Biochem., 64 (12), 2559-2568 (2000)). Others were produced by the fungus *Aspergillus nidulans* (DE102006006893).

It was reported in various articles and in patent literature that they exhibit a pronounced biological activity against *Artemia salina*, which is the brine shrimp. These are species of aquatic crustaceans of the genus *Artemia*, the only genus in the family Artemiidae of the order Anostraca (fairy shrimp, not closely related to true shrimp). Brine Shrimp have existed since the Triassic period of the Earth's existence, and have evolved little since. They are found worldwide in saltwater, though not in oceans. An anti-proliferating/cytotoxic activity is mentioned, for example, in the German patent DE102006006893. A nematicidal activity against the free living nematode *Caenorhabditis elegans* has been reported in the above-referenced article in Biosci. Biotechnol. Biochem. The genus *Artemia* is a member of the family Artemiidae which belongs to the order Anostraca, which belongs to the huge Phylum Arthropoda.

Arthropods are typically classified into five subphyla, of which one is extinct:

1. Trilobites are a group of formerly numerous marine animals that died in the mass extinction at the end of the Permian-Triassic extinction event.
2. Chelicerates include spiders, ticks, mites, scorpions and related organisms. They are characterized by the presence of chelicerae.
3. Myriapods comprise millipedes and centipedes and their relatives and have many body segments, each bearing one or two pairs of legs. They are sometimes grouped with the hexapods.
4. Hexapods comprise insects and three small orders of insect-like animals with six thoracic legs. They are sometimes grouped with the myriapods, in a group called Uniramia, though genetic evidence tends to support a closer relationship between hexapods and crustaceans.
5. Crustaceans are primarily aquatic (a notable exception being woodlice) and are characterized by having biramous appendages. They include lobsters, crabs, barnacles, crayfish, shrimp and many others.

So far no other activity for naturally occurring dihydroquinolinone derivatives other than against shrimp and helminths has been verified. Dihydroquinolinone derivatives with a similar substitution pattern as the natural products described herein are unknown.

PCT application WO200226713 describes substances that are produced by chemical means and belong to the chemical class of 1H-quinolin-2-ons. No biological activity is exemplified for said substances.

The present invention therefore in one aspect concerns the use of a dihydroquinolinone derivative of the formula I

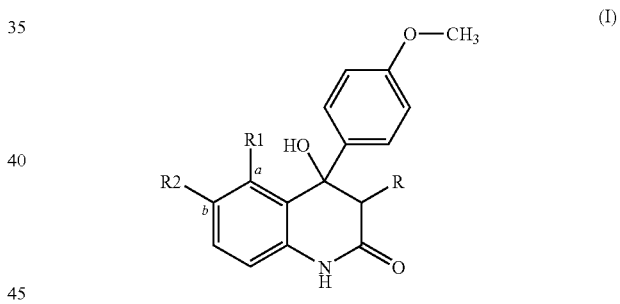

wherein
R is OH or OCH$_3$;
R1 is H or OH;
R2 is H or one of the following side chains

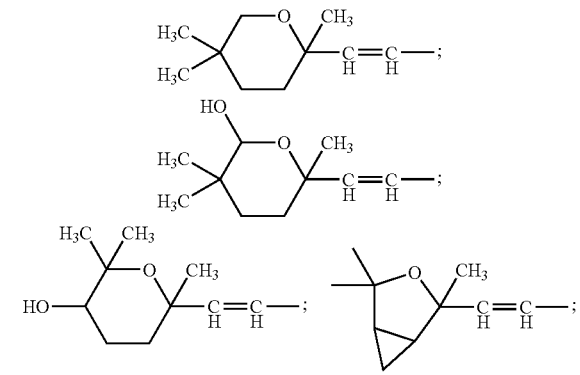

-continued

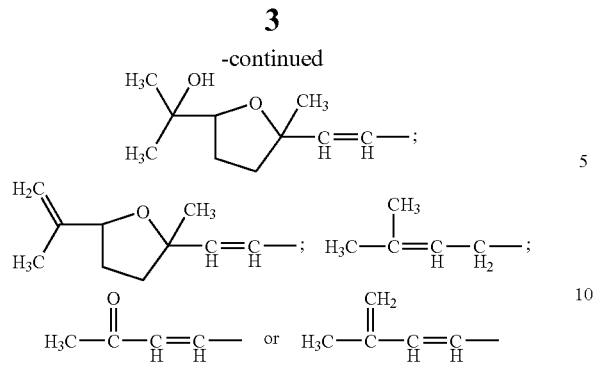

or the group R1- and the substituent R2- form together with the carbon atoms a and b of the phenyl group to which they are attached the following substituent

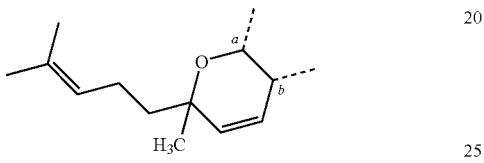

and the stereoisomers thereof, and whereby said compounds are in free form or salt form, for combating ectoparasites on non-human animals, and especially for combating ticks on farm animals or pet animals.

Salts of compounds of the formula I may be produced in known manner. Acid addition salts, for example, are obtainable from compounds I by treating with a suitable acid or a suitable ion exchange reagent, and salts with bases are obtainable by treating with a suitable base or a suitable ion exchange reagent.

Salts of compounds of the formula I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds of the formula I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds of the formula I with salt-forming characteristics can be obtained in free form or in the form of salts.

Specific but non-limiting examples of compounds of the formula I are the compounds nos. 1 to 13 shown below.

The use of the following group of the compounds nos. 1 to 13 as well as each individual compound no. 1 to no. 13 within the formula I is a preferred embodiment of the present invention.

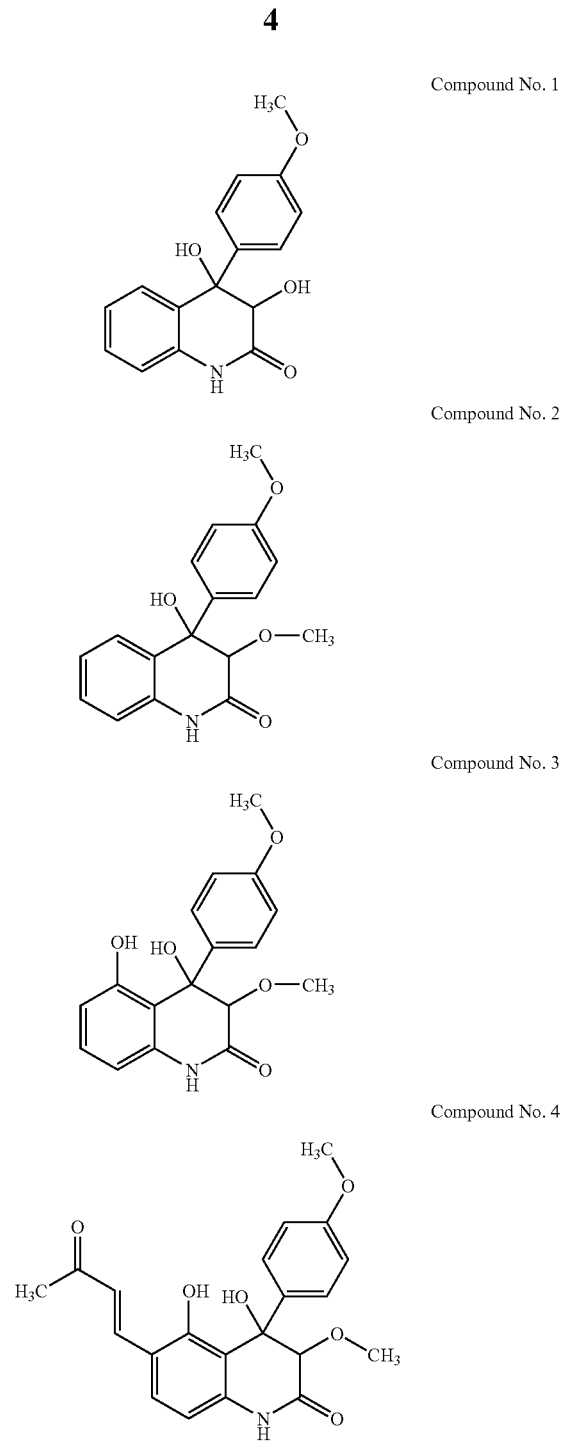

Compound No. 1

Compound No. 2

Compound No. 3

Compound No. 4

Compound No. 5

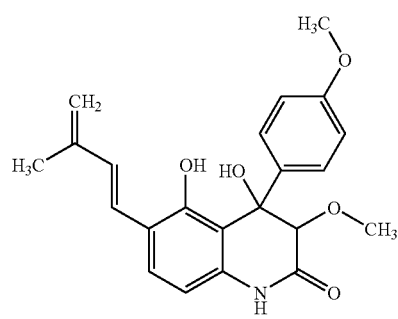

Compound No. 6

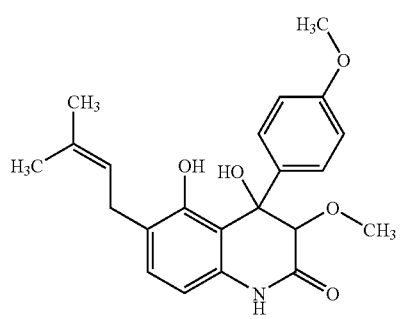

Compound No. 7

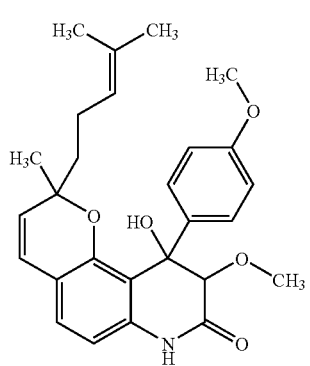

Compound No. 8

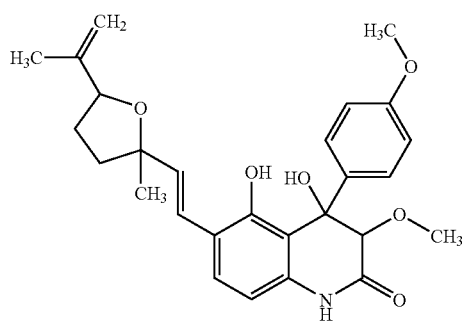

Compound No. 9

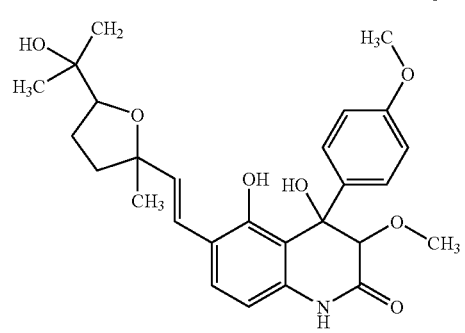

Compound No. 10

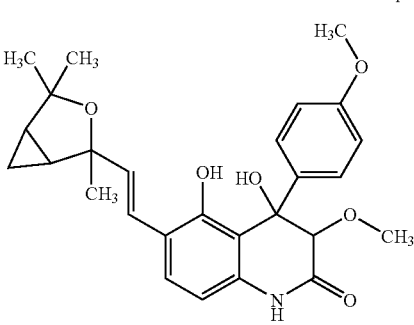

Compound No. 11

Compound No. 12

Compound No. 13 and

Within the formula I, the use of the compound No. 8 and particularly of compound No. 11 is especially preferred because of the pronounced tickicidal activity.

The compounds of the formula I contain several asymmetric carbon atoms or stereo centers. Consequently, the compounds of the formula I may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned.

Diastereoisomeric mixtures of compounds of the formula I, which are obtainable, may be separated in known manner, on the basis of the physical-chemical differences in their components, into the pure diastereoisomers, for example by fractional crystallization, distillation and/or chromatography.

Splitting of mixtures of enantiomers, that are obtainable accordingly, into the pure isomers, may be achieved by known methods, for example by recrystallization from an optically active solvent, by chromatography on chiral adsorbents, e.g. high-pressure liquid chromatography (HPLC) on acetyl cellulose, with the assistance of appropriate microorganisms, by cleavage with specific immobilized enzymes, through the formation of inclusion compounds, e.g. using chiral crown ethers, whereby only one enantiomer is complexed.

According to the invention, apart from separation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesize the biologically more active isomer, e.g. enantiomer, provided that the individual components have differing biological efficacy.

It has now surprisingly been found that the compounds of formula (I) and the individual representatives as defined above exhibit a pronounced activity against a series of ectoparasites on non-human animals, for example against representatives of the order acarina including ticks and mites, especially against ticks. They also exhibit a decent activity against blood-sucking insects, in particular fleas such as dog and cat fleas.

Examples of ectoparasites that infest non-human animals, without being limiting, are arthropod ectoparasites such as biting flies, blowflies, fleas, lice, other sucking insects or dipterous pests, ticks and mites. Examples of genera of such ectoparasites infecting animals and/or humans are *Aedes, Amblyomma, Boophilus, Calliphora, Chorioptes, Cochliomyia, Ctenocephalides, Culicoides, Damalinia, Demodex, Dermacentor, Dermanyssus, Dermatobia, Gasterophilus, Haematobia, Haematopinus, Haemaphysalis, Hyalomma, Hypoderma, Ixodes, Linognathus, Lucilia, Melophagus, Oestrus, Otobius, Otodectes, Phlebotomus, Psorergates, Psoroptes, Rhipicephalus, Sarcoptes, Stomoxys* and *Tabanus*.

The activity against Acarina, and especially against ticks, is the most pronounced activity of the compounds of the formula I. Acarina enclose parasites, such as mites (e.g. *Chorioptes bovis, Cheyletiella* spp., *Dermanyssus gaffinae, Demodex canis, Sarcoptes scabiei, Psoroptes ovis* and *Psorergates* spp.) and ticks.

In the context of the present invention, ticks are understood to be members of the order Acarina. Well-known representatives are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, horses, pigs, sheep and goats, poultry such as chickens, turkeys and geese, fur-bearing animals such as mink, foxes, chinchillas, rabbits and the like, as well as pets such as cats and dogs, but they can also infest humans.

Ticks may be divided into soft and hard ticks. Soft ticks have five immature stages and can infest several animals. They are short time blood feeders and the females have several blood meals after which they lay each time a few hundred eggs. Hard ticks are characterized by infesting one, two or three host animals. They attach themselves to a passing host animal and suck the blood or body fluids. Fully engorged female ticks drop from the host animal and lay large amounts of eggs (2000 to 3000) in a suitable crack in the floor or in any other protected site where the larvae hatch. These in turn seek a host animal, in order to suck blood from it. Larvae of ticks which only infest one host animal mould twice and thus become nymphs and finally adult ticks without leaving the host they have selected. Larvae of ticks which infest two or three host animals leave the animal after feeding on the blood, mould in the local environment and seek a second or third host as nymphs or as adult ticks, in order to suck its blood.

Ticks are responsible world-wide for the transmission and spread of many human and animal diseases. Because of their economic influence, the most important ticks are *Boophilus, Rhipicephalus, Ixodes, Hyalomma, Amblyomma* and *Dermacentor*. They are carriers of bacterial, viral, rickettsial and protozoal diseases and cause tick-paralysis and tick-toxicosis.

Even a single tick can cause paralysis whereby its saliva penetrates into the host animal during ingestion. Beside directly causing diseases, ticks can also transmit a wide range of so called TBDs (tick borne diseases). Such diseases, for example babesiosis, anaplasmosis, theileriosis and heart water disease, are responsible for the death or impairment of a large number of domestic and farm animals in the entire world. In many countries of temperate climate, *Ixodes* ticks transmit the agent of the chronically harmful Lyme's disease from wild animals to humans. Apart from the transmission of diseases, the ticks are responsible for great economic losses in livestock production. Losses are not confined to the death of the host animals, but also include damage to the pelts, loss of growth, a reduction in milk production and reduced value of the meat. Although the harmful effects of a tick infestation on animals have been known for years, and enormous progress has been made using tick-control programs, until now no completely satisfactory methods of controlling or eliminating these parasites have been found. In addition, ticks have often developed resistance to chemical active ingredients.

The good tickicidal action of the compounds of the formula I according to the invention corresponds to a kill rate (mortality) of at least 50-60%. In particular, the individually listed compounds of the formula I are characterized by a long duration of action and are well tolerated by the host animal if applied in a tickicidally effective amount.

The good pesticidal activity of the compounds of formula I according to the invention corresponds to a mortality rate of at least 50-60% of the pests mentioned, more preferably to a mortality rate over 90%, most preferably to 95-100%. The compounds of formula I are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e.g. capsules, powders including soluble powders, granules, embeddings of the active ingredient in polymeric substances, like implants and microparticles). As with the compositions, the methods of application are selected in accordance with the intended objectives and the prevailing circumstances.

The formulation, i.e. preparations containing the active ingredient of formula I, or combinations of these active ingredients with other active ingredients, and optionally a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be, for example: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, ketones, such as propylene carbonate, cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpalmitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application forms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™, saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers, polyvinyl alcohols, polyvinylpyrrolidons and fine disperse silicium dioxide.

As polymeric agents with controlled release properties, may be applied derivatives made by e.g. polylactic acid, polylactic coglycolic acid, poly orthoester, polyethylene carbonate, poly anhydrids and starch and PVC based matrices.

The addition of penetration enhancers like ketons, sulfoxids, amids, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may be also applied in capsules, like hard gelatin capsules or soft capsules.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants (e.g. magnesium stearate) and disintegrants (e.g. cellulose derivatives) and acid resistant coatings, like e.g. acrylic acid esters.

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. By combining the compounds of the formula I with other suitable parasiticides not only the parasiticidal activity can be enhanced but the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

| | |
|---|---|
| 1. | Abamectin |
| 2. | Acephate |
| 3. | Acequinocyl |
| 4. | Acetamiprid |
| 5. | Acetoprole |
| 6. | Acrinathrin |
| 7. | AKD-1022 |
| 8. | Alanycarb |
| 9. | Aldicarb |
| 10. | Aldoxycarb |
| 11. | Allethrin |
| 12. | Alpha-cypermethrin |
| 13. | Alphamethrin |
| 14. | Amidoflumet |
| 15. | Amitraz |
| 16. | Anabasine |
| 17. | Avermectin B1 |
| 18. | Azadirachtin |
| 19. | Azamethiphos |
| 20. | Azinphos-ethyl |
| 21. | Azinphos-methyl |
| 22. | Azocyclotin |
| 23. | *Bacillus subtil.* toxin |
| 24. | *Bacillus thuringiensis* |
| 25. | Benclothiaz |
| 26. | Bendiocarb |
| 27. | Benfuracarb |
| 28. | Bensultap |
| 29. | Benzoximate |
| 30. | Beta-cyfluthrin |
| 31. | Beta-cypermethrin |
| 32. | Bifenazate |
| 33. | Bifenthrin |
| 34. | Bioallethrin |
| 35. | Bioresmethrin |
| 36. | Bistrifluron |
| 37. | BPMC |
| 38. | Brofenprox |
| 39. | Bromophos A |
| 40. | Bromopropylate |
| 41. | Bufencarb |

| | -continued | | | -continued |
|---|---|---|---|---|
| 42. | Buprofezin | | 122. | Fenthion |
| 43. | Butocarboxim | | 123. | Fenvalerate |
| 44. | Cadusafos | | 124. | Fipronil |
| 45. | Carbaryl | | 125. | Flonicamid |
| 46. | Carbofuran | | 126. | Fluacrypyrim |
| 47. | Carbophenothion | | 127. | Fluazinam |
| 48. | Carbosulfan | | 128. | Fluazuron |
| 49. | Cartap | | 129. | Flubendiamide |
| 50. | Chloethocarb | | 130. | Flucycloxuron |
| 51. | Chlorantraniliprole | | 131. | Flucythrinate |
| 52. | Chlorethoxyfos | | 132. | Flufenerim |
| 53. | Chlorfenapyr | | 133. | Flufenoxuron |
| 54. | Chlorfenvinphos | | 134. | Flufenprox |
| 55. | Chlorfluazuron | | 135. | Flumethrin |
| 56. | Chlormephos | | 136. | Fonophos |
| 57. | Chlorpyrifos | | 137. | Formothion |
| 58. | Chlorpyrifos-methyl | | 138. | Fosthiazate |
| 59. | Chromafenozide | | 139. | Fubfenprox |
| 60. | Cis-Resmethrin | | 140. | Furathiocarb |
| 61. | Clofentezin | | 141. | Gamma-cyhalothrin |
| 62. | Clothianidin | | 142. | Halfenprox |
| 63. | Coumaphos | | 143. | Halofenozide |
| 64. | Cyanophos | | 144. | HCH |
| 65. | Cycloprothrin | | 145. | Heptenophos |
| 66. | Cyenopyrafen | | 146. | Hexaflumuron |
| 67. | Cyflumetofen | | 147. | Hexythiazox |
| 68. | Cyfluthrin | | 148. | Hydramethylnon |
| 69. | Cyhalothrin | | 149. | Hydroprene |
| 70. | Cyhexatin | | 150. | Imidacloprid |
| 71. | Cymiazole | | 151. | Imiprothrin |
| 72. | Cypermethrin | | 152. | Indoxacarb |
| 73. | Cyphenothrin | | 153. | insect-active fungi |
| 74. | Cyromazine | | 154. | insect-active nematodes |
| 75. | Deltamethrin | | 155. | insect-active viruses |
| 76. | Demeton M | | 156. | Iprobenfos |
| 77. | Demeton S | | 157. | Isofenphos |
| 78. | Demeton-S-methyl | | 158. | Isoprocarb |
| 79. | Diafenthiuron | | 159. | Isoxathion |
| 80. | Diazinon | | 160. | Ivermectin |
| 81. | Dichlofenthion | | 161. | Karanjin |
| 82. | Dichlorvos | | 162. | Kinoprene |
| 83. | Dicofol | | 163. | Lamba-Cyhalothrin |
| 84. | Dicrotophos | | 164. | Lepimectin |
| 85. | Dicyclanil | | 165. | Lufenuron |
| 86. | Diethion | | 166. | Malathion |
| 87. | Diflovidazin | | 167. | Mecarbam |
| 88. | Diflubenzuron | | 168. | Mesulfenphos |
| 89. | Dimefluthrin | | 169. | Metaflumizone |
| 90. | Dimethoate | | 170. | Metaldehyde |
| 91. | Dimethylvinphos | | 171. | Methamidophos |
| 92. | Dinobuton | | 172. | Methidathion |
| 93. | Dinocap | | 173. | Methiocarb |
| 94. | Dinotefuran | | 174. | Methomyl |
| 95. | Diofenolan | | 175. | Methoprene |
| 96. | Dioxathion | | 176. | Methothrin |
| 97. | Disulfoton | | 177. | Methoxyfenozide |
| 98. | DNOC | | 178. | Metofluthrin |
| 99. | Doramectin | | 179. | Metolcarb |
| 100. | DPX-HGW86 | | 180. | Metoxadiazone |
| 101. | Edifenphos | | 181. | Mevinphos |
| 102. | Emamectin | | 182. | Milbemectin |
| 103. | Empenthrin | | 183. | Milbemycin oxime |
| 104. | Endosulfan | | 184. | Monocrotophos |
| 105. | Esfenvalerat | | 185. | Moxidectin |
| 106. | Ethiofencarb | | 186. | Naled |
| 107. | Ethion | | 187. | Nicotine |
| 108. | Ethiprole | | 188. | Nitenpyram |
| 109. | Ethoprophos | | 189. | Novaluron |
| 110. | Etofenprox | | 190. | Noviflumuron |
| 111. | Etoxazole | | 191. | Omethoate |
| 112. | Etrimphos | | 192. | Oxamyl |
| 113. | Fenamiphos | | 193. | Oxydemethon M |
| 114. | Fenazaquin | | 194. | Oxydeprofos |
| 115. | Fenbutatin oxid | | 195. | Parathion |
| 116. | Fenitrothion | | 196. | Parathion-methyl |
| 117. | Fenobucarb | | 197. | Permethrin |
| 118. | Fenothiocarb | | 198. | Phenothrin |
| 119. | Fenoxycarb | | 199. | Phenthoate |
| 120. | Fenpropathrin | | 200. | Phorate |
| 121. | Fenpyroximate | | 201. | Phosalone |

| | |
|---|---|
| 202. | Phosmet |
| 203. | Phosphamidon |
| 204. | Phoxim |
| 205. | Pirimicarb |
| 206. | Pirimiphos A |
| 207. | Pirimiphos M |
| 208. | Polynactins |
| 209. | Prallethrin |
| 210. | Profenofos |
| 211. | Profluthrin |
| 212. | Promecarb |
| 213. | Propafos |
| 214. | Propargite |
| 215. | Propoxur |
| 216. | Prothiofos |
| 217. | Prothoate |
| 218. | Protrifenbute |
| 219. | Pymetrozine |
| 220. | Pyrachlofos |
| 221. | Pyrafluprole |
| 222. | Pyresmethrin |
| 223. | Pyrethrin |
| 224. | Pyrethrum |
| 225. | Pyridaben |
| 226. | Pyridalyl |
| 227. | Pyridaphenthion |
| 228. | Pyrifluquinazon |
| 229. | Pyrimidifen |
| 230. | Pyriprole |
| 231. | Pyriproxyfen |
| 232. | Quinalphos |
| 233. | Resmethrin |
| 234. | Rotenone |
| 235. | RU 15525 |
| 236. | Sabadilla |
| 237. | Salithion |
| 238. | Selamectin |
| 239. | Silafluofen |
| 240. | Spinetoram |
| 241. | Spinosad |
| 242. | Spirodiclofen |
| 243. | Spiromesifen |
| 244. | Spirotetramat |
| 245. | Sulcofuron sodium |
| 246. | Sulfluramid |
| 247. | Sulfotep |
| 248. | Sulfur |
| 249. | Sulprofos |
| 250. | Tau-fluvalinate |
| 251. | Tebufenozide |
| 252. | Tebufenpyrad |
| 253. | Tebupirimfos |
| 254. | Teflubenzuron |
| 255. | Tefluthrin |
| 256. | Temephos |
| 257. | Terbufos |
| 258. | Tetrachlorvinphos |
| 259. | Tetradifon |
| 260. | Tetramethrin |
| 261. | Thiacloprid |
| 262. | Thiamethoxam |
| 263. | Thiocyclam |
| 264. | Thiodicarb |
| 265. | Thiofanox |
| 266. | Thionazin |
| 267. | Thiosultap |
| 268. | Thuringiensin |
| 269. | Tolfenpyrad |
| 270. | Tralomethrin |
| 271. | Transfluthrin |
| 272. | Triarathene |
| 273. | Triazamate |
| 274. | Triazophos |
| 275. | Trichlorfon |
| 276. | Triflumuron |
| 277. | Trimethacarb |
| 278. | Vamidothion |
| 279. | Vaniliprole |
| 280. | XMC (3,5,-Xylylmethylcarbamate) |
| 281. | Xylylcarb |
| 282. | Zeta-cypermethrin |
| 283. | Zetamethrin |
| 284. | ZXI 8901 |

Non-limitative examples of suitable anthelmintics are named in the following, a few representatives have anthelmintic activity in addition to the insecticidal and acaricidal activity. Some of them are already listed above.

| | |
|---|---|
| (A1) | Abamectin |
| (A2) | Albendazole |
| (A3) | Cambendazole |
| (A4) | Closantel |
| (A5) | Diethylcarbamazine |
| (A6) | Doramectin |
| (A7) | Emodepside |
| (A8) | Eprinomectin |
| (A9) | Febantel |
| (A10) | Fendendazole |
| (A11) | Flubendazole |
| (A12) | Ivermectin |
| (A13) | Levamisol |
| (A14) | Mebendazole |
| (A15) | Milbemectin |
| (A16) | Milbemycin Oxime |
| (A17) | Morantel |
| (A18) | Moxidectin |
| (A19) | Nitroscanate |
| (A20) | Omphalotin |
| (A21) | Oxantel |
| (A22) | Oxfendazole |
| (A23) | Oxibendazole |
| (A24) | Phenothiazine |
| (A25) | Piperazine |
| (A26) | PNU-97333 |
| (A27) | PNU-141962 |
| (A28) | Praziquantel |
| (A29) | Pyrantel |
| (A30) | Thiabendazole |
| (A31) | Triclabendazole |
| amino acetonitrile derivatives named in WO2005044784 | |

Non-limitative examples of suitable repellents and detachers are:
(R1) DEET (N,N-diethyl-m-toluamide)
(R2) KBR 3023 N-butyl-2-oxycarbonyl-(2-hydroxy)-piperidine
(R3) Cymiazole=N,-2,3-dihydro-3-methyl-1,3-thiazol-2-ylidene-2,4-xylidene Non-limitative examples of suitable synergists are:

| |
|---|
| (S1) Piperonyl butoxide |
| (S2) Ethylenediaminetetraacetic acid |
| (S2) Cyclodextrin |
| (S4) Piprotal |
| (S5) Propyl isome |
| (S6) Sesamex |
| (S7) Sesamolin |
| (S8) Sulfoxide |
| (S9) Tribufos |

Synergists S1 to S9 are well-known or can be found in the Internet, for example, in the Compendium of Pesticide Common Names. Synergists are compounds which increase the action of the active compounds without it being necessary for the synergist added to be active itself.

The above-specified combination partners are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

The commercially available compounds described in the table above can be found in The Pesticide Manual, 14th Ed. (2006), The British Crop Protection Council, London except for 99, 160, 183, 185, 238, A2, A6, A8, A9, A10, A12, A13, A16, A17, A18, A22, A23, A25, A28, A29, A30, which are described in the Compendium of Veterinary Products, 9th Ed. (2006), North American Compendiums, Inc. Compounds Nos. 5, 7, 14, 66, 67, 100, 132, 163, 218, 221, 228, 230, 240, 244, 268, and 279 can be found in the Internet, for example, in the online Merck Veterinary Manual and Compendium of Pesticide Common Names. 154: a preparation which contains insect-active nematodes, preferably *Heterorhabditis bacteriophora* and *Heterorhabditis megidis*, from The Pesticide Manual, 11th Ed. (1997), The British Crop Protection Council, London, page 671; *Steinernema feltiae*, from The Pesticide Manual, 11th Ed. (1997), The British Crop Protection Council, London, page 1115 and *Steinernema scapterisci*, from The Pesticide Manual, 11th Ed. (1997), The British Crop Protection Council, London, page 1116;
153: a preparation which contains insect-active fungi, preferably *Verticillium lecanii*, from The Pesticide Manual, 11th Ed. (1997), The British Crop Protection Council, London, page 1266; *Beauveria brogniartii*, from The Pesticide Manual, 11th Ed. (1997), The British Crop Protection Council, London, page 85 and *Beauveria bassiana*, from The Pesticide Manual, 11th Ed. (1997), The British Crop Protection Council, London, page 83; 155: a preparation which contains insect-active viruses, preferably *Neodipridon Sertifer* NPV, from The Pesticide Manual, 11th Ed. (1997), The British Crop Protection Council, London, page 1342; *Mamestra brassicae* NPV, from The Pesticide Manual, 11th Ed. (1997), The British Crop Protection Council, London, page 759 and *Cydia pomonella granulosis* virus, from The Pesticide Manual, 11th Ed. (1997), The British Crop Protection Council, London, page 291.

As a consequence of the above details, a further essential aspect of the present invention relates to combination preparations for the control of parasites on warm-blooded animals, characterized in that they contain, in addition to a compound of formula I, at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of active ingredient of formula I, or mixtures thereof, 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present in the form of solutions, emulsions, suspensions, (drenches), powders, tablets, boli, capsules, collars, ear tags and pour-on formulations.

Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to 1 ml per kg, preferably about 0.1 ml per kg, with a total volume from 1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid distribution over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 40%, preferably 10 to 25% by weight of a compound of formula I, 0 to 50% by weight of dispersing agent and 10 to 99%, preferably 45 to 90% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favored by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates.

Such compositions may also contain further additives, such as stabilizers, anti-foaming agents, viscosity regulators, binding agents or tackifiers, as well as other active ingredients, in order to achieve special effects.

Insecticidal and acaricidal compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method for prophylactically protecting animals, especially productive livestock, domestic animals and pets, against parasites which is characterized in that the active ingredients of formula I or the active ingredient formulations prepared therefrom are administered to the animals as an additive to the feed, or to the drinks or also in solid or liquid form, orally, as pour-on or spot-on, by injection or parenterally. The invention also includes the compounds of formula I according to the invention for usage in one of the said processes.

The following examples illustrate the invention further, the term active ingredient representing a substance listed in table 1.

In particular, preferred formulations are made up as follows:
(%=percent by weight)

FORMULATION EXAMPLES

1. Granulate

|  | a) | b) |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

2. Granulate

| active ingredient | 3% |
| --- | --- |
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

3. Tablets or Boil

| I | active ingredient | 33.00% |
| --- | --- | --- |
|  | methylcellulose | 0.80% |
|  | silicic acid, highly dispersed | 0.80% |
|  | corn starch | 8.40% |
| II | lactose, cryst. | 22.50% |
|  | corn starch | 17.00% |
|  | microcryst. cellulose | 16.50% |
|  | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.
III The preliminary mixes obtained according to I and II are mixed and pressed into tablets or boli.

4. Injectables

| A. Oily vehicle (slow release) | | |
| --- | --- | --- |
| 1. | active ingredient | 0.1-1.0 g |
|  | groundnut oil | ad 100 ml |
| 2. | active ingredient | 0.1-1.0 g |
|  | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 μm.

| B Water-miscible solvent (average rate of release) | |
| --- | --- |
| active ingredient | 0.1-1.0 g |
| 4-hydroxymethyl-1,3-dioxolane (glycerol formal) | 40 g |
| 1,2-propanediol | ad 100 ml |
| active ingredient | 0.1-1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 μm.

| C. Aqueous solubilisate (rapid release) | | |
| --- | --- | --- |
| 1. | active ingredient | 0.1-1.0 g |
|  | polyethoxylated castor oil (40 ethylene oxide units) | 10 g |
|  | 1,2-propanediol | 20 g |
|  | benzyl alcohol | 1 g |
|  | aqua ad inject. | ad 100 ml |
| 2. | active ingredient | 0.1-1.0 g |
|  | polyethoxylated sorbitan monooleate (20 ethylene oxide units) | 8 g |
|  | 4-hydroxymethyl-1,3-dioxolane (glycerol formal) | 20 g |
|  | benzyl alcohol | 1 g |
|  | aqua ad inject. | ad 100 ml |

Preparation: The active ingredient is dissolved in the solvents and the surfactant, and made up with water to the desired volume. Sterile filtration through an appropriate membrane filter of 0.22 μm pore size.

5. Pour on

| A. | |
| --- | --- |
| active ingredient | 5 g |
| isopropyl myristate | 10 g |
| isopropanol | ad 100 ml |
| B. | |
| active ingredient | 2 g |
| hexyl laurate | 5 g |
| medium-chained triglyceride | 15 g |

-continued

| | | |
|---|---|---|
| ethanol | ad 100 ml | |
| C. | | |
| active ingredient | 2 g | |
| oleyl oleate | 5 g | |
| N-methyl-pyrrolidone | 40 g | |
| isopropanol | ad 100 ml | |

6. Spot on

| A. | |
|---|---|
| active ingredient | 10-15 g |
| diethyleneglycol monoethylether | ad 100 ml |
| B. | |
| active ingredient | 10-15 g |
| octyl palmitate | 10 g |
| isopropanol | ad 100 ml |
| C. | |
| active ingredient | 10-15 g |
| isopropanol | 20 g |
| benzyl alcohol | ad 100 ml |

7 Spray on

| A. | |
|---|---|
| active ingredient | 1 g |
| isopropanol | 40 g |
| propylene carbonate | ad 100 ml |
| B. | |
| active ingredient | 1 g |
| propylene glycol | 10 g |
| isopropanol | ad 100 ml |

The aqueous systems may also preferably be used for oral and/or intraruminal application.

The compositions may also contain further additives, such as stabilizers, e.g. where appropriate epoxidized vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula I and do not have a harmful effect on the host animal to be treated, as well as mineral salts or vitamins, may also be added to the described compositions.

If the tickicidal compositions are present in the form of feed concentrates, then high-performance feed, feed cereals or protein concentrates, for example, are used as carriers.

Such feed concentrates or compositions can, in addition to the active ingredients, also comprise additives, vitamins, antibiotics, chemotherapeutics, or other pesticides, mainly bacteriostats, fungistats, coccidiostats, or also hormone preparations, anabolics or substances which promote growth, influence the quality of meat from animals for slaughter or are useful to the organism in another way. If the compositions or the active ingredients of the formula I present therein are added directly to the feed or to the drinking water for the animals, the finished feed or the finished drinking water comprises the active ingredients preferably in a concentration from approximately 0.0005 to 0.02% by weight (5-200 ppm).

The following examples serve to illustrate the invention. The starting substances used may be produced by methods described in literature or are commercially available.
Preparation of Compounds No. 5 to 9 and 11

The filamentous fungus *Penicillium scabrosum* (e.g. CBS-305.97) is grown in 500 ml flasks containing 250 ml of a liquid medium consisting of malt extract (20 g/L), Glucose (20 g/L) and Peptone (1 g/L). After 3 days of incubation at 24° C. at 150 rpm, these cultures are used to inoculate production flasks containing Rice grains or a liquid medium. The liquid medium consist of Soymeal (20 g/L) and Mannitol (20 g/L) and is adjusted to a pH7 prior to sterilisation. Cultivation is carried out at 24° C. for 10 to 30 days without agitation. The fermentation broth is harvested and subsequently extracted with an organic solvent like Methanol or Ethylacetate. The raw extract is purified via silica gel chromatography using Heptan and Ethylacetate (50:50). Fractions containing the compounds of formula I are evaporated to dryness and reconstituted in Acetonitril. Final purification is done via chromatography on a C18 reversed phase column using a Water Acetonitril gradient.

Biological Examples

Control of Animal Parasites

The following test methods are employed in investigating the acaricidal and insecticidal action of the compounds of the formula I.

1. Activity In Vitro Against *Ctenocephalides felis* (Cat Flea).

A mixed adult population of fleas is placed in a suitably formatted 96-well plate allowing fleas to access and feed on treated blood via an artificial feeding system. Each compound is tested by serial dilution in order to determine its minimal effective dose (MED). Fleas are fed on treated blood for 24 hours, after which the compound's effect is recorded. Insecticidal activity is determined on the basis of the number of dead fleas recovered from the feeding system.

For example, compound No. 11 shows in this test at 32 ppm a mean efficacy of 95%, compound No. 8 shows at 100 ppm a mean efficacy of 90%, compound No. 9 shows at 63 ppm a mean efficacy of 70%.

2. Activity In Vitro Against Ticks 5-10 ticks of different species (i.e. *Rhipicephalus sanguineus, Dermacentor* spp., etc.) are distributed into a microplate pre-coated with test compound. Each compound is tested by serial dilution in order to determine its Minimal Effective Dose (MED). The microplates are then incubated at 28° C. and 80% humidity until evaluation. At different time points, ticks are excited by carbon dioxide flush and/or heat. If in reaction to the stimulation, ticks start moving, the test compound is scored as inactive at the tested concentration.

If the ticks fail to respond to the stimulation, they are considered dead and the compound is scored as active at the tested concentration. Activity is calculated as a percentage of dead ticks compared to untreated controls.

For example, compound No. 11 shows in this test at 10 ppm a mean efficacy of 100% against *Rhipicephalus sanguineus* and *Dermacentor variabilis* and at 32 ppm a mean efficacy of 90% against *Amblyomma variegatum*.

3. Activity In Vitro Against *Dermanyssus gallinae*

A clean female mite population is used to seed a suitably formatted 96-well plate containing the test substances to be evaluated for antiparasitic activity. Each compound is tested by serial dilution in order to determine its Minimal Effective Dose (MED). Mites are left in contact with the test compound for 10 minutes and are then incubated at 25° C. and 60% relative humidity (RH) for 5 days, during which the test compound's effect is monitored. Acaricidal activity is confirmed if mites are dead without having laid eggs. Egg-laying and ensuing mite development are also recorded to identify possible growth-regulating activity. For example, compound No. 11 shows in this test at 63 ppm a mean efficacy of 90%.

4. In-Vivo Test Against *Rhipicephalus sanguineus* Nymphs on Mongolian Gerbils (*Meriones unguiculatus*)

On day 0, gerbils are treated with the test compound at a given dose by spray (or spot-on) application. On day +1 (+2), the animals are infested with nymphs of *Rhipicephalus. sanguineus*. Ticks are left on the animals until full repletion. Seven days after infestation nymphs dropped off fully engorged are collected and counted. They are kept until molting to also evaluate growth regulating activity of the test compound. Efficacy in killing (and growth regulating) is expressed as a tick number (and molted tick number) reduction in comparison with a placebo treated group, using the Abbot's formula.

For example, compound No. 8 shows in this test at 10 ppm a mean efficacy of 60%, and compound No. 11 shows at 3.2 ppm a mean efficacy of 95%.

5. In-Vivo Test Against Ticks (*Rhipicephalus sanguineus*) on Dogs

Dogs of the beagle breed are separated into one treatment and one control group (4 dogs per group). On day 0, the dogs are treated with the test compound at a dose of 25 mg/kg (15% solution in Transcutol) by spot-on application (between the shoulder blades). On day +1, the animals are infested with unfed adult ticks (sex ratio 1:1). Evaluation of efficacy is performed at 48 h, and then weekly 48 h after reinfestation with ticks by counting the numbers of dead and live ticks recovered from the animals. Efficacy is expressed as comparison with a placebo treated group using the Abbot's formula. Infestation can be repeated at weekly intervals until efficacy drops.

For example, compound No. 11 shows in this test activity above 90% for six weeks.

6. In-Vivo Test Against Ticks (*Ixodes ricinus*) on Cats

Cats are separated into one treatment and one control group (4 cats per group). On day 0, the cats are treated with the test compound at a dose of 25 mg/kg (1% solution in Polypropylenglycol) by spray application. On day +1, the animals are infested with unfed adult ticks (sex ratio 1:1). Evaluation of efficacy is performed at 48 h, and then weekly 48 h after reinfestation with ticks by counting the numbers of dead and live ticks recovered from the animals. Efficacy is expressed as comparison with a placebo treated group using the Abbot's formula. Infestation can be repeated at weekly intervals until efficacy drops. For example, compound No. 11 shows in this test 95% activity after one week and 70% activity after two weeks.

Preferred embodiments within the present invention are:

(A1) The use of a compound of the formula I

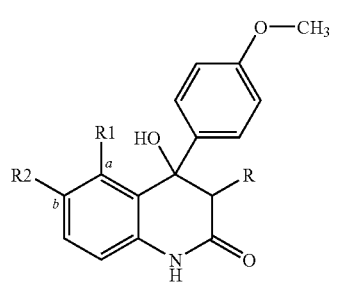

wherein
R is OH or $OCH_3$;
R1 is H or OH;
R2 is H or one of the following side chains

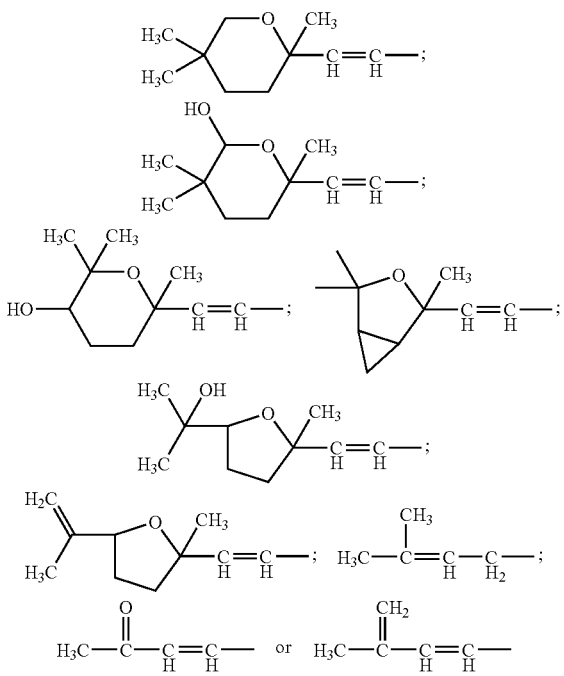

or the group R1- and the substituent R2- form together with the carbon atoms a and b of the phenyl group to which they are attached the following substituent

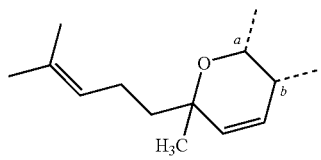

and the stereoisomers thereof, and whereby said compounds are in free form or salt form for combating ectoparasites on non-human animals, and especially for combating ticks on farm animals or pets animals.

(A2) The use of a compound of the formula I as defined under A1 characterized in that
R is $OCH_3$;
R1 is OH;
R2 is one of the following side chains

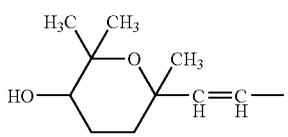

and the stereoisomers thereof, in free form or salt form for combating ectoparasites on non-human animals, and especially for combating ticks on farm animals or pets animals.

(B1) The use of

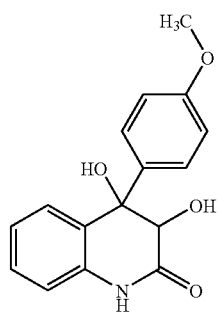

Compound No. 1 and the stereoisomers thereof, in free form or salt form for combating ectoparasites on non-human animals, and especially for combating ticks on farm animals or pets animals.

(B2) The use of

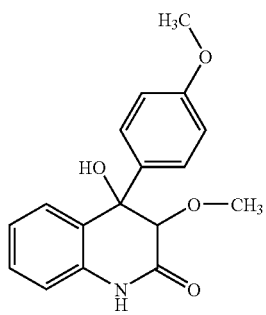

Compound No. 2 and the stereoisomers thereof, in free form or salt form for combating ectoparasites on non-human animals, and especially for combating ticks on farm animals or pets animals.

(B3) The use of

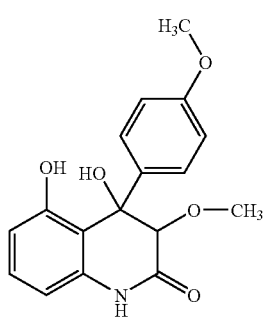

Compound No. 3 and the stereoisomers thereof, in free form or salt form for combating ectoparasites on non-human animals, and especially for combating ticks on farm animals or pets animals.

(B4) The use of

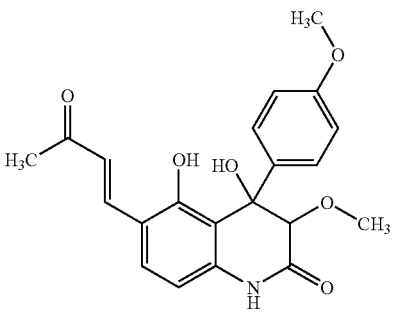

Compound No. 4 and the stereoisomers thereof, in free form or salt form for combating ectoparasites on non-human animals, and especially for combating ticks on farm animals or pets animals.

(B5) The use of

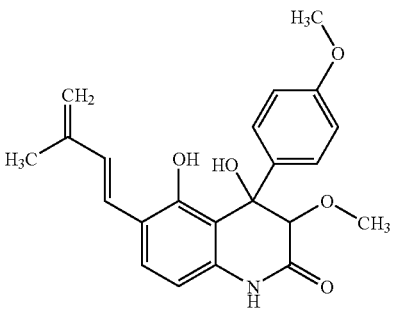

Compound No. 5 and the stereoisomers thereof, in free form or salt form for combating ectoparasites on non-human animals, and especially for combating ticks on farm animals or pets animals.

(B6) The use of

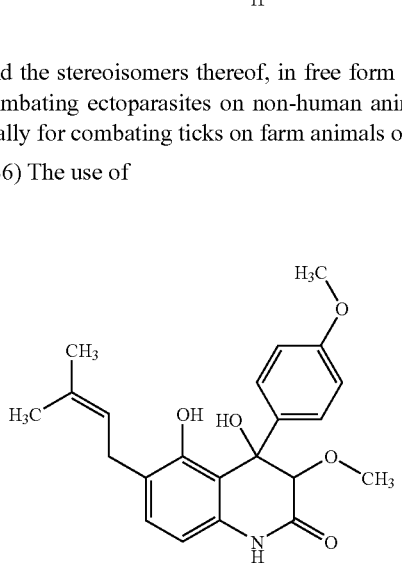

Compound No. 6 and the stereoisomers thereof, in free form or salt form for combating ectoparasites on non-human animals, and especially for combating ticks on farm animals or pets animals.

(B7) The use of

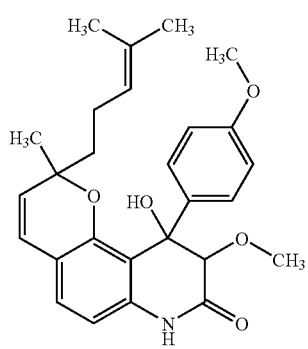

Compound No. 7 and the stereoisomers thereof, in free form or salt form for combating ectoparasites on non-human animals, and especially for combating ticks on farm animals or pets animals.

(B8) The use of

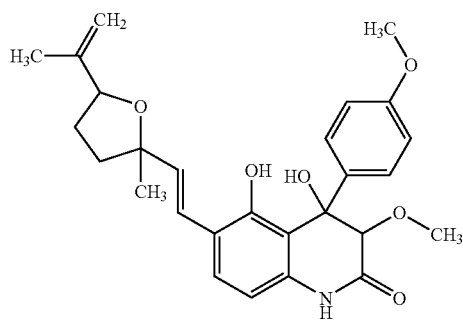

Compound No. 8 and the stereoisomers thereof, in free form or salt form for combating ectoparasites on non-human animals, and especially for combating ticks on farm animals or pets animals. Compound 8 is one of the most preferred compounds.

(B9) The use of

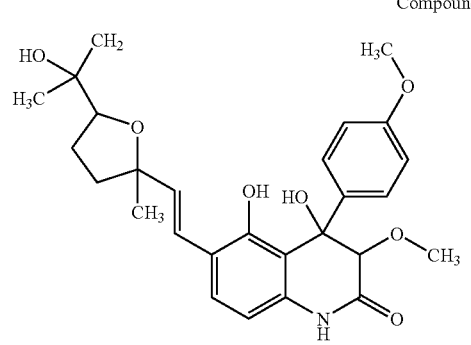

Compound No. 9 and the stereoisomers thereof, in free form or salt form for combating ectoparasites on non-human animals, and especially for combating ticks on farm animals or pets animals.

(B10) The use of

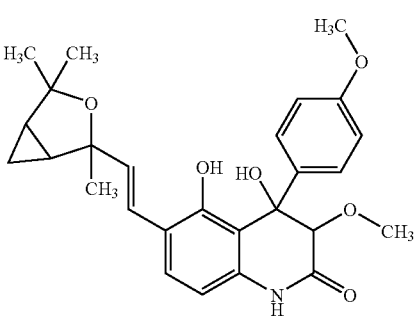

Compound No. 10 and the stereoisomers thereof, in free form or salt form for combating ectoparasites on non-human animals, and especially for combating ticks on farm animals or pets animals.

(B11) Especially preferred is the use of

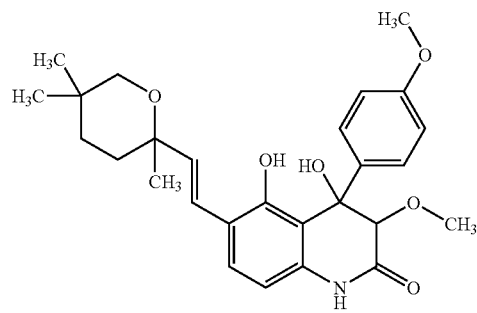

Compound No. 11 and the stereoisomers thereof, in free form or salt form for combating ectoparasites on non-human animals, and especially for combating ticks on farm animals or pets animals. Compound II is the most preferred compound because of its pronounced activity.

(B12) The use of

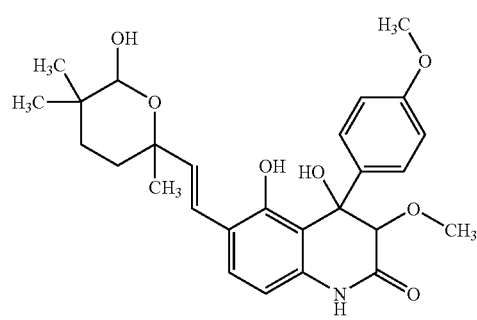

Compound No. 12 and the stereoisomers thereof, in free form or salt form for combating ectoparasites on non-human animals, and especially for combating ticks on farm animals or pets animals.

(B13) The use of

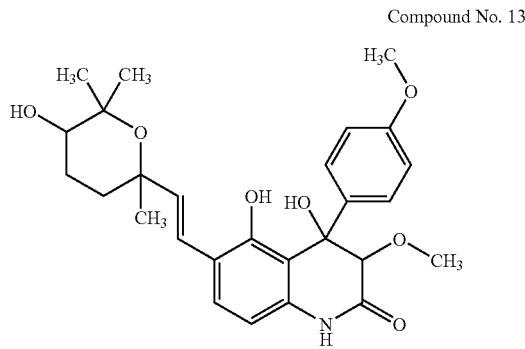 [SMILES: COc1ccc(C2(O)c3c(ccc(/C=C/C4(C)CCC(O)C(C)(C)O4)c3O)NC(=O)C2OC)cc1]

Compound No. 13 and the stereoisomers thereof, in free form or salt form for combating ectoparasites on non-human animals, and especially for combating ticks on farm animals or pets animals.

(C) The use as defined under A1, A2 and B1 to B13 characterized in that the compound of the formula I is a racemate, a mixture of stereoisomers or a pure enantiomer in free form or salt form.

(D) The use as defined under A1, A2 and B1 to B13 characterized in that the ectoparasites are acarina, preferably ticks or mites and especially ticks.

(E) The use as defined under A1, A2 and B1 to B13 characterized in that the ectoparasites are insects, preferably fleas.

(F) Ectoparasiticidal composition comprising a compound of the formula I as defined in A1, A2 and B1 to B13 together with a carrier or diluent that is physiologically acceptable to non-human animals.

(G1) Composition according to F characterized in that the ectoparasites are acarina, preferably ticks or mites and especially ticks.

(G2) Composition according to F characterized in that the ectoparasites are insects, preferably fleas.

(H) Composition according to F, G1 or G2 consisting of a pour-on or spot-on formulation.

(I) Method of controlling ectoparasites on non-human animals, characterized in that an effective amount of at least one compound of formula I as defined in A1, A2 and B1 to B13 is administered to the habitat of the parasites.

(K1) Method according to (I) characterized in that the ectoparasites are acarina, preferably ticks or mites and especially ticks.

(K2) Method according to (I) characterized in that the ectoparasites are insects, preferably fleas.

(L) Use of a compound of the formula I as defined in A1, A2 and B1 to B13 for the preparation of an ectoparasiticidal composition according to claim 6.

(M) Compound of the formula I as defined in A1, A2 and B1 to B13 for the use in the treatment of ectoparasites on non-human animals, preferably acarina or insects, most preferably ticks.

(N) Use of a compound of the formula I as defined in A1, A2 and B1 to B13 in the manufacture of a veterinary composition for combating ectoparasites on non-human animals, preferably a veterinary composition for combating acarina or insects, most preferably ticks.

What is claimed is:

1. A method of controlling ticks on a non-human animal, comprising applying topically and/or locally to the animal a tickicidally effective amount of the compound of the formula

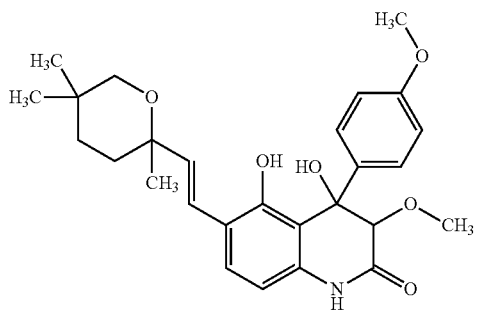

Compound No. 11 or a stereoisomer thereof, which compound is in free form or salt form.

2. The method of claim 1 wherein the tickicidally effective amount of Compound No. 11 is 25 mg/kg.

3. The method of claim 1 wherein a pour-on or spot-on formulation is applied topically and/or locally to the animal.

* * * * *